United States Patent
Ljungberg

(10) Patent No.: US 11,497,865 B2
(45) Date of Patent: Nov. 15, 2022

(54) COMPUTER CONTROLLED DOSAGE SYSTEM

(71) Applicant: Medituner AB, Stockholm (SE)

(72) Inventor: Henrik Ljungberg, Stockholm (SE)

(73) Assignee: Medituner AB, Stockholm (SE)

( * ) Notice: Subject to any disclaimer, the term of this patent is extended or adjusted under 35 U.S.C. 154(b) by 399 days.

(21) Appl. No.: 15/508,949

(22) PCT Filed: Sep. 16, 2014

(86) PCT No.: PCT/EP2014/069665
§ 371 (c)(1),
(2) Date: Mar. 6, 2017

(87) PCT Pub. No.: WO2016/041576
PCT Pub. Date: Mar. 24, 2016

(65) Prior Publication Data
US 2017/0262613 A1    Sep. 14, 2017

(51) Int. Cl.
*A61M 15/00* (2006.01)
*G16H 40/67* (2018.01)
(Continued)

(52) U.S. Cl.
CPC ............ *A61M 15/00* (2013.01); *A61B 5/4839* (2013.01); *A61M 15/0066* (2014.02);
(Continued)

(58) Field of Classification Search
CPC .. G06F 19/00; G06F 19/3456; G06F 19/3418; A61M 15/00; A61M 15/0066;
(Continued)

(56) References Cited

U.S. PATENT DOCUMENTS 5,363,842 A * 11/1994 Mishelevich ........ A61B 8/0875
128/200.14
5,487,378 A * 1/1996 Robertson ......... A61M 15/0065
128/200.14
(Continued)

FOREIGN PATENT DOCUMENTS

WO    WO-2005087091 A2 *  9/2005  ............ A61B 5/0002
WO    WO-2010110682 A1 *  9/2010  ........ A61M 15/0065
(Continued)

OTHER PUBLICATIONS

Hernández, Marugán J., "International Search Report," prepared for PCT/EP2014/069665, dated Jul. 27, 2015, four pages.
(Continued)

*Primary Examiner* — Fonya M Long
*Assistant Examiner* — Alaaeldin M Elshaer
(74) *Attorney, Agent, or Firm* — Shackelford, Bowen, McKinley & Norton, LLP

(57) ABSTRACT

Disclosed is a computer controlled dosage system, for dosage adjustment for a mobile, hand held, inhaler for delivering a dosage of a medicine, is provided. The system comprises at least one measuring device for measuring at least one parameter; and a handheld mobile computer separate from the inhaler, the computer being configured to communicate with the at least one measuring device and with a remote memory for sending and receiving information to and from patient medical records of the remote memory for storage in a memory of the computer, and the computer being configured to receive a manual input for storage in the memory of the computer. The computer is configured to create a data set for setting a plurality of levels of different dosages of medicine based on the medicine used by the inhaler, the information from the patient's medical records of the remote memory, and the manual input; and the computer is further configured to store the data set in the
(Continued)

memory of the computer. The computer is further configured to generate an indication indicating a dosage adjustment for the inhaler, based on the at least one parameter and on one of the plurality of levels of dosage of the data set, the indication indicating one of the plurality of levels of dosage of the data set as the dosage adjustment for the inhaler. A dosage regime generated by the computer controlled dosage system is also disclosed.

14 Claims, 1 Drawing Sheet

(51) Int. Cl.
  *G16H 20/10* (2018.01)
  *A61B 5/00* (2006.01)
  *G16H 40/63* (2018.01)
(52) U.S. Cl.
  CPC .... *A61M 15/0068* (2014.02); *A61M 15/0083* (2014.02); *G16H 20/10* (2018.01); *A61M 15/009* (2013.01); *A61M 2202/0275* (2013.01); *A61M 2202/064* (2013.01); *A61M 2205/332* (2013.01); *A61M 2205/3303* (2013.01); *A61M 2205/3331* (2013.01); *A61M 2205/3375* (2013.01); *A61M 2205/3553* (2013.01); *A61M 2205/3561* (2013.01); *A61M 2205/3569* (2013.01); *A61M 2205/3584* (2013.01); *A61M 2205/3592* (2013.01); *A61M 2205/50* (2013.01); *A61M 2205/502* (2013.01); *A61M 2205/505* (2013.01); *A61M 2205/52* (2013.01); *A61M 2205/581* (2013.01); *A61M 2205/583* (2013.01); *A61M 2230/20* (2013.01); *A61M 2230/201* (2013.01); *A61M 2230/205* (2013.01); *A61M 2230/43* (2013.01); *A61M 2230/46* (2013.01); *G16H 40/63* (2018.01); *G16H 40/67* (2018.01)
(58) Field of Classification Search
  CPC .......... A61M 15/0068; A61M 15/0083; A61M 11/00; A61M 2202/0275; A61M 2205/3331; A61M 2230/20; A61M 2230/201; A61M 2205/52; A61M 2230/43; A61B 5/00; A61B 5/4839; A61B 5/87; A61B 5/08; A61B 5/145; A61B 5/09; A61B 5/097; A61B 5/087; A61B 5/091; A61K 39/395; G16H 20/10; G16H 40/63; G16H 40/67
  USPC ........................................................ 705/2, 3
  See application file for complete search history.

(56) References Cited

U.S. PATENT DOCUMENTS

| | | | | |
|---|---|---|---|---|
| 6,089,227 | A * | 7/2000 | Nilsson | A61M 15/0065 128/203.15 |
| 6,684,879 | B1 * | 2/2004 | Coffee | B05B 5/0255 128/200.14 |
| 9,138,167 | B1 * | 9/2015 | Leydon | A61B 5/087 |
| 2001/0037083 | A1 * | 11/2001 | Hartlaub | G16H 20/17 604/65 |
| 2002/0079309 | A1 * | 6/2002 | Cox | A61M 11/041 219/486 |
| 2002/0189615 | A1 * | 12/2002 | Henry | A61M 15/0045 128/203.21 |
| 2003/0036683 | A1 * | 2/2003 | Kehr | G06F 19/325 600/300 |
| 2004/0123864 | A1 * | 7/2004 | Hickey | A61M 15/0085 128/203.12 |
| 2007/0239058 | A1 * | 10/2007 | Krasilchikov | G01F 1/3259 600/538 |
| 2008/0022998 | A1 * | 1/2008 | Hamano | A61M 11/041 128/200.14 |
| 2008/0178872 | A1 * | 7/2008 | Genova | A61M 15/0065 128/200.23 |
| 2009/0156952 | A1 | 6/2009 | Hunter et al. | |
| 2009/0294521 | A1 | 12/2009 | de la Huerga | |
| 2010/0018524 | A1 * | 1/2010 | Jinks | A61M 15/009 128/200.23 |
| 2010/0078015 | A1 * | 4/2010 | Imran | A61M 11/007 128/200.23 |
| 2010/0094099 | A1 * | 4/2010 | Levy | A61M 15/009 600/300 |
| 2010/0108062 | A1 * | 5/2010 | Ganem | A61M 15/0028 128/203.21 |
| 2012/0247235 | A1 * | 10/2012 | Adamo | A61B 5/08 73/865.4 |
| 2012/0328606 | A1 * | 12/2012 | Gossage | G01N 33/56972 424/133.1 |
| 2014/0206949 | A1 * | 7/2014 | Lucas | G16H 40/67 600/301 |
| 2014/0261414 | A1 * | 9/2014 | Weitzel | A61M 15/002 128/203.14 |
| 2015/0077737 | A1 * | 3/2015 | Belinsky | G01N 21/53 356/51 |
| 2015/0269348 | A1 * | 9/2015 | Madjd | G16H 40/67 705/3 |
| 2016/0198980 | A1 * | 7/2016 | Tchernichovsky | A61B 5/0876 600/539 |
| 2016/0325057 | A1 | 11/2016 | Morrison et al. | |
| 2019/0385727 | A1 * | 12/2019 | Manice | A61M 15/008 |

FOREIGN PATENT DOCUMENTS

| | | | | |
|---|---|---|---|---|
| WO | WO-2014106056 | A2 * | 7/2014 | A61M 5/31 |
| WO | WO-2015189700 | A1 * | 12/2015 | H04W 4/90 |

OTHER PUBLICATIONS

Licskai, Christopher J., et al.; "Development and pilot testing of a mobile health solution for asthma self-management: Asthma action plan smartphone application pilot study"; Can Respir J, vol. 20, No. 4; Jul. 2013; pp. 301-306.

Van Der Meer, Victor, et al.; "Internet-Based Self-management Plus Education Compared With Usual Care in Asthma"; Annals of Internal Medicine, vol. 151, No. 2; Jul. 21, 2009; pp. 110-120, W-27-W-31.

* cited by examiner

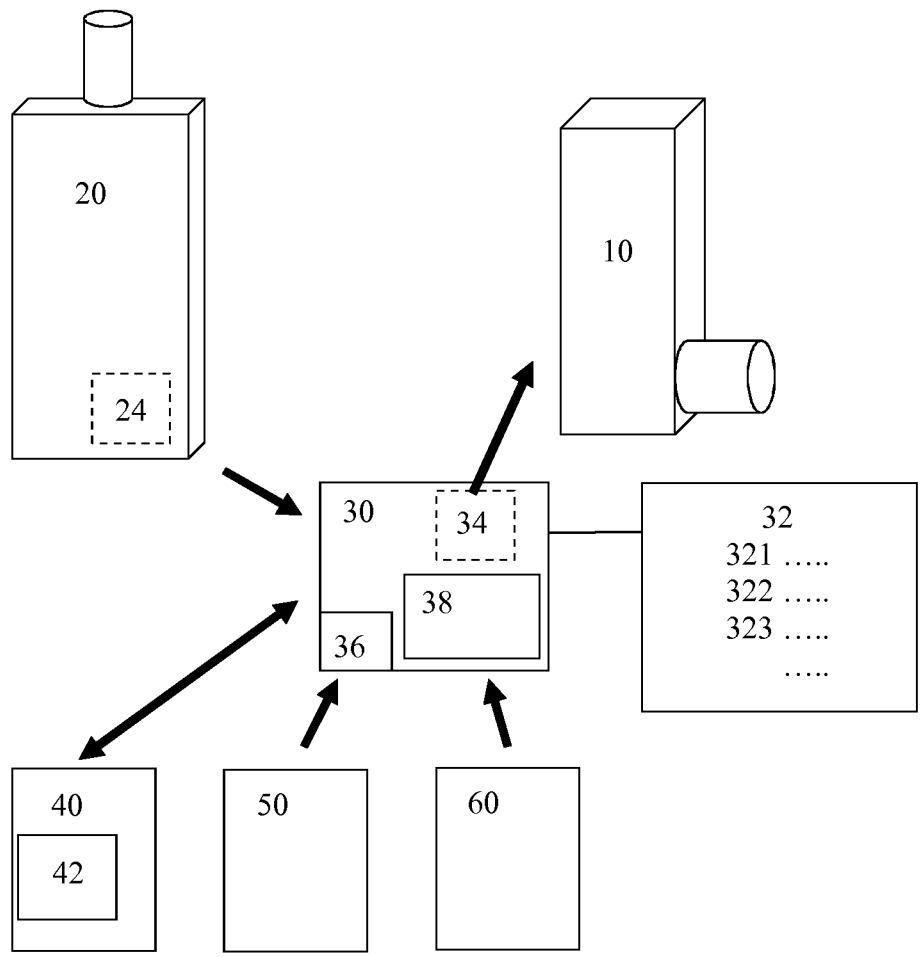

COMPUTER CONTROLLED DOSAGE SYSTEM

TECHNICAL FIELD

The present disclosure relates to a dosage device. More particularly, the present disclosure relates to a computer controlled dosage system for administering pharmaceutical compounds and a dosage regime for the same. The dosage device may be an inhaler.

BACKGROUND

In recent years attention has been turned to inhalers. Inhalers are normally used by a patient in a manner that has been prescribed by a doctor. While this provides satisfactory results in everyday life, it would be desirable to tailor inhaled dosage as you go along. A higher dosage may be desirable under certain conditions. A lower dosage may be desirable under other conditions. It is a problem how to adjust the dosage to inhale according to the patient's present condition or changes.

It is a problem how to adjust the inhaled dosage according to the patient's environment.

An inhaler is a device that delivers a fixed dosage of medicine. It is a problem to adjust the dosage when necessary. For example, when to adjust the dosage is not known to an average patient. What conditions justifies an adjustment of the dosage and what is the amount of the adjustment is not known to a patient. How much the dosage should be adjusted, up or down, is not known to an average patient. While a patient may take more inhalations or less inhalations the adjustment of the dosage is not known to the patient. It is a problem to adjust the dosage so that not too much medication is used, but also so that not too little medication is used. Too much medication (overmedicating) is not good in the long run and too little medication (undermedicating) will not be sufficient to reach therapeutic effect for the patient.

A technical restriction is the existing inhalers on the marked and the desire to provide a system that is compatible with such inhalers. Furthermore, the systems in place and national law and restriction concerning medical dosage systems put a limitation on what can be done. To improve evidence-based care, it is desirable, also by a National Board of Health and Welfare to address problems such as: close follow-up and regular symptom monitoring; regular measurements of lung function; increased education of health care staff and patients; and individualized treatment plans for all patients. It is a problem how to automate this so that more patients can have their individual treatment plans according to recommendations and, in addition, how it can be provided so that they have it with them wherever they may need it. The recommended regular measurement of lung function is time consuming and expensive as it has to be performed several times before and after medication at a clinic by a trained nurse, and afterwards the result has to be interpreted by a physician.

The present invention is directed to overcoming one or more of the problems as set forth above.

SUMMARY

It is an object of the present invention to provide a computer controlled dosage system. This object can be achieved by the features as defined by the independent claims. Further enhancements are characterized by the dependent claims.

It is an object of the present invention to provide a dosage regime for a computer controlled dosage system. This object can be achieved by the features of the independent claims. Further enhancements are characterized by the dependent claims.

According to one embodiment, a computer controlled dosage system, for dosage adjustment for a mobile, hand held, inhaler for delivering a dosage of a medicine, is provided. The system comprises at least one measuring device for measuring at least one parameter; and a handheld mobile computer separate from the inhaler, the computer being configured to communicate with the at least one measuring device and with a remote memory for sending and receiving information to and from patient medical records of the remote memory for storage in a memory of the computer, and the computer being configured to receive a manual input for storage in the memory of the computer. The computer is configured to create a data set for setting a plurality of levels of different dosages of medicine based on the medicine used by the inhaler, the information from the patient's medical records of the remote memory, and the manual input; and the computer is further configured to store the data set in the memory of the computer. The computer is further configured to generate an indication indicating a dosage adjustment for the inhaler, based on the at least one parameter and on one of the plurality of levels of dosage of the data set, the indication indicating one of the plurality of levels of dosage of the data set as the dosage adjustment for the inhaler.

According to one embodiment, the computer may further be configured to receive an automatic input and the configuration for generating the indication further is based on the automatic input. The automatic input may be one or more of the following group: pollen levels, air pollution, weather conditions, biological parameter, pollen index, lung volume, air flow to or from lung, blood sample, blood sugar level, body weight, body surface area, environmental condition, humidity, air pressure, height above sea level, GPS position, recent or future user activity, nutrition intake, or user data.

According to one embodiment, the measuring device may be one or more of the following group: a spirometer, an accelerometer, a pulse oximeter, an impulse oscillometer (IOS), a blood sample device, a flow meter for lungs, a peak flow meter, a device sampling marker of inflammation, and/or a device sampling marker of inflammation from exhaled air.

According to one embodiment, the indication may be a text and/or graphic message on a screen of the computer. The indication may be a dosage adjustment by one of the following adjustments or by a combination of one or more of the following adjustments: adjusting the amount of medicine delivered at each inhalation; adjusting the frequency of inhalations; adjusting the number of inhalations; and adjusting by adding a further medicine.

According to one embodiment, the computer is a mobile phone and the configuration of the computer is an application on the mobile phone or an application in an internet cloud.

According to one embodiment, the system further comprises a reminding system to communicate when a dosage should be taken, preferably the communication is made via a phone, a mobile phone, a smartphone, sms, or an e-mail.

According to one embodiment, the parameter is added manually by the user to the system, and/or the system is configured to collect information and/or parameters from a user's electronic diary, wherein the information from a user's electronic diary comprises past, present, and future information regarding one or more of the following group: gym visits, exercises, and location.

According to one embodiment, the at least one measuring device is configured to measure markers of inflammation from the airway of a user, preferably a fraction of exhaled Nitric Oxide (FeNO), and the system is configured to use this as the parameter to adjust the dosage of the inhaler.

According to one embodiment, the computer is further configured for providing reports or logged information regarding the user's condition based on the at least one measured parameter for adjusting the dosage.

According to one embodiment, the inhaler is configured to provide a dosage of insulin for the treatment of diabetes.

According to one embodiment, the inhaler is a powder dose metered inhaler, an aerosol form inhaler, a nebulised form inhaler, or any kind of dosage delivery apparatus.

According to one embodiment, the computer is further configured to limit the dosage for the purpose of not adjusting the dosage to a dangerous dosage or to a non-affective dosage, avoiding under- or overmedication.

According to one embodiment, a dosage regime for a dosage system as disclosed herein wherein a dosage of medicine is adjusted to one of the plurality of levels of dosage of the data set.

According to one embodiment, a computer controlled inhaler system, for dosage adjustment, may comprise an inhaler for delivering a dose (dosage) of medicine; at least one measuring device for measuring at least one parameter; and a computer in communication with the at least one measuring device; wherein the computer indicates a dosage adjustment for the inhaler based on the at least one parameter.

According to one embodiment, a dosage regime for an inhaler system may adjust a dosage of medicine of the inhaler according to the at least one parameter. At least one of the above embodiments provides one or more solutions to the problems and disadvantages with the background art. Other technical advantages of the present disclosure will be readily apparent to one skilled in the art from the following description and claims. Various embodiments of the present application obtain only a subset of the advantages set forth. No one advantage is critical to the embodiments. Any claimed and/or described embodiment herein may be technically combined with any other claimed and/or described embodiment(s).

BRIEF DESCRIPTION OF THE DRAWINGS

The accompanying drawings illustrate presently preferred exemplary embodiments of the disclosure, and together with the general description given above and the detailed description of the preferred embodiments given below, serve to explain, by way of example, the principles of the disclosure.

FIG. 1 is a diagrammatic illustration of some exemplary embodiments of the present disclosure.

DETAILED DESCRIPTION

FIG. 1 illustrated a computer controlled dosage system, for example a computer controlled inhaler system. This system is suitable for dosage adjustment for a mobile, hand held, inhaler (10) for delivering a dosage of a medicine. The inhaler (10) may be a purely mechanical inhaler, without any electronic components. The system comprises at least one measuring device (20) for measuring at least one parameter (24). This may for example be a spirometer allowing measurement of lung function and providing such a measurement as a parameter (24) to the system.

The system comprises a handheld mobile computer (30). This may for example be a mobile smart phone. The computer (30) is separate from the inhaler (10). The dosage deliverer (10), inhaler (10), does not comprise a computer. This allows the system to work with any inhaler (10). The computer (30) is configured to communicate with the at least one measuring device (20). The computer (30) is further configured to communicate with a remote memory (40) for sending and receiving information (42) to and from patient medical records of the remote memory (40). This allows for a two way communication between the remote memory (40) and the computer (30). The remote memory (40) is not part of the computer (30) or the inhaler (10) and is, for example, a large central data base comprising patient data. This information (42) may be stored in a memory (36) of the computer (30). The computer (30) is also configured to receive a manual input (50), and this input (50) may be stored in the memory (36) of the computer (30).

The computer (30) is configured to create a data set (32) for setting a plurality of levels of different dosages (321, 322, 323) of medicine. This data set (32) may be a treatment plan according to national requirements or legislation. The configuration of this data set (32) is based on the medicine used by the inhaler (10), the information (42) from the patient's medical records of the remote memory (40), and the manual input (50). This allows the computer to create a data set that comprises a plurality of different levels, e.g. green (321), yellow (322), and red (323), of different dosages of the medicine tailored to a user, but also according to the patient's medical records, the medicine and answers to questions asked by the computer (manual input), and technically fulfilling national requirements or legislation. Thus, the configuration for creating the data set (32) can be a pre-set condition, such as a national standard or regulation. The plurality of levels of different dosages of medicine can be any number, for example, 2, 3, 4, 5, 6, 7, 8, 9, or more. The computer (30) may further be configured to store the data set (32) in the memory (36) of the computer (30).

The computer (30) is further configured to generate an indication (34). This indication (34) is indicating a dosage adjustment for the dosage system, the inhaler (10), based on the at least one parameter (24) and on one of the plurality of levels of dosage (321, 322, 323) of the data set. The indication (34) is indicating one of the pluralities of levels of dosage (321, 322, 323) of the data set (32) as the dosage adjustment for the inhaler (10).

In one embodiment, which may apply to the entire disclosure, the computer (30) may have a processor. The configuring the computer may be done by configuring the processor of the computer (30).

A technical effect of the computer controlled dosage system, as claimed in claim 1, is given by how the different components (20, 30) are arranged and how they are connected, and the way the computer (30) has been configured. This allows the system to technically provide the data set (32) and technically define the different levels of dosage (321, 322, 323). It is this technical configuration of the system that achieves the data set to be generated, not merely defined, and useful for dosage adjustment. Important is that the system is configured to adapt the data set (32) to the national legislation or other predetermined rules, making it technically possible to use the system in real life and integrate the system in the national health care system.

Furthermore, the arrangement of the different components (20, 30) of the system, how they are connected, can communicate, and how they are configured, allows the system to provide an indication of the dosage. This indication may be a level of dosage from the data set. This indication may, as an example and in a simple form, be a text message, and allows the dosage system, e.g. an inhaler, to give an adjusted dosage, not too much or too little (overmedicating or undermedicating).

According to one embodiment, the computer (30) may further be configured to receive an automatic input (60) and the configuration for generating the indication (34) may further be based on the automatic input (60). Such an automatic input (60) may be one or more of the following group: pollen levels, air pollution, weather conditions, biological parameter, pollen index, lung volume, air flow to or from lung, blood sample, blood sugar level, body weight, body surface area, environmental condition, humidity, air pressure, height above sea level, GPS position, recent or future user activity, nutrition intake, or user data. The computer may be configured such that the automatic input may be pulled in via the internet or any other accessible remote data.

According to one embodiment, the indication (34) may be a text and/or graphic message on a screen (38) of the computer (30). The computer (32) may indicate, e.g. on a screen or by sound, the adjustment to the dosage and the user may make the adjustment. The indication (34) may be a dosage adjustment by one of the following adjustments or by a combination of one or more of the following adjustments: adjusting the amount of medicine delivered at each inhalation; adjusting the frequency of inhalations; adjusting the number of inhalations; and adjusting by adding a further medicine. For example, a dosage adjustment could be moving from a first level of two inhalations every morning and evening to a second level of three inhalations every morning, midday, and evening. For example, a dosage adjustment can be effected by subsequent actuation of the dosage system, the inhaler. The system may be configured to provide the user of the inhaler with information how to adjust the dosage of the inhaler. For example, the system may inform the user that two inhalations should be taken rather than only one inhalation each time. For example the system may inform the user that six inhalations should be taken within 24 hours, rather than only four inhalations. This would allow a user to take the correct dosage, thus allowing the dosage of the medication to be taken in the most effective way for the user.

According to one embodiment, the measuring device (20) may be one or more of the following group: a spirometer, an accelerometer, a pulse oximeter, an impulse oscillometer (IOS), a blood sample device, a flow meter for lungs, a peak flow meter, a device sampling marker of inflammation, and/or a device sampling marker of inflammation from exhaled air.

According to one embodiment, the computer (30) is a mobile phone and the configuration of the computer (30) is an application on the mobile phone or an application in an internet cloud. The computer may be a part of a smart phone, tablet, or similar. The configuration of the computer may be the configuration of a processor within the computer. The configuration may be done by an application and by providing any necessary hardware.

According to one embodiment, the system may further comprise a reminding system to communicate when a dosage should be taken; preferably the communication is made via a phone, a mobile phone, a smartphone, sms, or an e-mail. This may ensure that a dosage is actually taken, or at least noted.

According to one embodiment, the parameter (24) is added manually by the user to the system, and/or the system is configured to collect information and/or parameters from a user's electronic diary, wherein the information from a user's electronic diary comprises past, present, and future information regarding one or more of the following group: gym visits, exercises, and location. For example, if a user has been to the gym, entering that into a dairy, or manually directly into the system, the system may be configured to take account of that information when generating the indication for dosage adjustment.

According to one embodiment, the at least one measuring device (20) may be configured to measure markers of inflammation from the airway of a user, preferably a fraction of exhaled Nitric Oxide (FeNO). Additionally, the system may be configured to use this as the parameter to adjust the dosage indication for the inhaler.

According to one embodiment, the computer may further be configured for providing reports or logged information regarding the user's condition based on the at least one measured parameter (24). This report may be displayed on the computer itself (on the screen (38)), and/or may be sent to the remote memory (40) for access by others, e.g. medical staff. This may allow for the system to be supervised according to national legislation. As a result, information may be sent back to the system, allowing a modification/improvement of the dosage system, e.g. by generating a modified data set (32) allowing for improved dosage adjustment.

According to one embodiment, the dosage delivery system, the inhaler (10), may be configured to provide a dosage of insulin for the treatment of diabetes. As such, the system may be suitable for any kind of medicine. According to one embodiment, the inhaler (10) may be a powder dose metered inhaler, an aerosol form inhaler, a nebulised form inhaler, or any kind of dosage delivery apparatus.

According to one embodiment, the computer (30) may be further configured to limit the dosage for the purpose of not adjusting the dosage to a dangerous dosage or to a non-affective dosage, avoiding under- or overmedication. This may depend on the medicine used and the medicine used may be input to the system as a manual input, thus the computer may be configured to receive a manual input of what medicine is used.

According to one embodiment, a dosage regime is disclosed for a dosage system as described herein with reference to any one embodiment or combination thereof, wherein a dosage of medicine is adjusted to one of the plurality of levels of dosage (321, 322, 323) of the data set (32). The system generates the data set (32) that comprises a plurality of levels of different dosages (321, 322, 323). The dosage regime comprises the system indicating what level of dosage should be taken by a user. As disclosed and explained herein, the system generates a dosage regime for the user and the medicine in question. In this way the dosage of the medicine may be given to a user resulting in the most effective dosage given, and avoiding giving a dangerous dosage or a non-affective dosage.

According to embodiments, the system may be configured to limit the dosage for the purpose of not adjusting the dosage to a dangerous dosage or to a non-affective dosage. This may be done to comply with health regulations and/or any attempted misuse of the inhaler (10).

According to at least one embodiment, the indication (34) may be no adjustment at all, thus maintaining the present dosage. This would indicate that the dosage used is the appropriate and effective dosage.

In one embodiment, the at least one measuring device (20) is configured to measure markers of inflammation from the airway of a user, preferably a fraction of exhaled Nitric Oxide (FeNO), and the system is configured to use this as the parameter to adjust the dosage of the inhaler.

At least one of the embodiments provides a computer controlled inhaler system with the objective to administer pharmaceutical compounds. It can contain medicine in powder form (powder dose metered inhaler), aerosol form, or nebulised form. The dose can be adjusted, allowing the dose of inhaled medicine to be increased or reduced, tailored, to that specific user's requirements. The dose adjustment function allows for optimisation of treatment by increasing or reducing the dose without delay when required. This also reduces the total amount of medicine administered. The system may comprise the administering device (powder dose metered inhaler, aerosol form or nebulised form) and may be used for all medical conditions where inhaled medicine is appropriate.

A dosage may be the amount of medicine given, the administration of medicine in doses, and/or the number or frequency of doses. Dosage may be the administration of a drug or agent in prescribed amounts and at prescribed intervals. Dosage may be the optimum therapeutic dose and optimum interval between doses. The dose may be electronically controlled via software that adjusts the administered dose depending on the at least one parameter. It may take a range of other factors into account when calculating the dose.

According to at least one embodiment, a computer controlled dosage system could also be used with conventional inhalers informing the user how many inhalations to take any day. An example of use is for users with asthma or chronic obstructive pulmonary disease (COPD), diseases that are characterised by variability where the dose may need rapid adjustment upwards or downwards. Another compound that may be administered via inhalation is insulin for the treatment of diabetes. For example, a dosage for diabetes may be adjusted each time taken.

Embodiments of the system software may have other uses such as for example: communicate with the patient's treating doctor or nurse to inform him/her of any exacerbation in the patient's condition; collect information from the internet or relevant institutions regarding environmental conditions such as weather, humidity, smog/fine particle levels, pollen levels and take these into account when calculating the dose. This information can be related to the user's geographical location as identified by gps or smartphone location as there may be local variations regarding proximity to heavy traffic or going to the countryside where pollen levels may be higher.

According to at least one embodiment, a user may make manual adjustments either by entering information by hand or letting the device collect information from the user's electronic diary about gym visits and/or exercise where the dosage may need adjustment.

According to at least one embodiment, the system may collect information from other devices measuring markers of disease. These devices can be anything from taking simple home blood tests to devices that measure markers of inflammation from the airway such as for example the fraction of exhaled Nitric Oxide (FeNO). The latter is useful for patients with allergic asthma. The collected information, parameters, may be used to adjust the dosage.

According to at least one embodiment, the system may provide reports or logged information for the benefit of treating medical staff or the user him or herself regarding the user's condition as well as compliance to medication.

According to at least one embodiment, the system may link with the user's medical records giving treating medical staff information about the user's condition and making dosage adjustments improving treatment.

Turning to some more specific embodiments, the computer controlled system overcomes one or more problems mentioned above by supporting self-management of the disease, improving communication between user and healthcare as well as making health care more efficient while also increasing the quality of clinical decisions. The system may be an easy-to-use self-management application with portable spirometry to enable healthcare to better follow guidelines without increasing number of visits while also reducing number of unplanned visits given that dosage can be adapted to variable factors over time (lung function, health condition, weather, pollen count etc.) and given that users' motivation to follow the dosage will increase. The user may take control over the disease and experience an increase in quality of life.

At least one embodiment may benefit asthma/COPD patients and care providers as well as specialized lung clinics. The may provide more timely and accurate diagnosis; more efficient organization of the clinical work; more focus on structured patient evaluation; increased capacity and competence of health care professionals, particular general practitioners; and improved user education and self-management programs.

At least one embodiment of the system may provide a user the possibility of self-monitoring and to achieve disease control. The user will get dosage recommendations based on variable factors without spending much time with the application. The dosage system, for example for asthma and COPD, may be arranged in relatively clear guidelines by international consensus. Specifically there are steps wherein the gathered information on symptoms, lung function, etc. may be transferred into information on dosage (e.g. frequency) of medication. The system will let a user or health care worker know clearly which dosage step they should be following and thereby improve individualized care. Tailored dosage leads to reduced risk of side effects. The system may also educate users in self-management and for example remind asthma patients to take the allergy medication when the pollen count of their specific allergy goes up. Potentially, the end result will be an empowered and motivated user achieving increased quality of life. The improved communication possibility benefits both healthcare and users. Healthcare can decide what information they want to collect from the system and how frequently. The most fundamental biological end marker that may be collected regularly is one or two lung function parameters. Seeing longitudinal changes of lung function may improve the quality of decisions made and in addition has valuable diagnostic and prognostic information. The user will be able to easily access an updated individual dosage plan if needed without visiting the primary care facility saving time and money for all involved.

According to one specific exemplary embodiment, the system may comprise a small lung function measurement device (a spirometer). The cost of this is comparable to very simple peak flow meters for home use. The spirometer can be used with a smartphone that will be configured by an application. The data collected by the system may be visible in the patient's medical records of the remote memory. The remote memory may be direct, or indirectly, via an internet based portal to the national health care. By doing this, information such as, for example, asthma or COPD, known allergies, medications, weight, and height will be entered into the app which can then establish a treatment plan according to national and international guidelines for every patient. The user will be able to measure their lung function themselves and will receive questions. This information collected by the system, together with information on for example pollen counts, air pollution and influenza epidemics, will generate an indication of the dosage. The system may send data to the health care provider so that for example lung function over time can be displayed in the medical record at the next visit at the health care provider. The possibility of contacting the health care system can also be used to automate procedures like booking appointments, requesting new prescriptions or similar.

According to one exemplary embodiment, the system may comprise a smart phone, a computer, configured to receive manual data input (for example, age, sex, anthropometrics, comorbidities, informed consent, answer burden symptoms and intake of dosage, schedule reminders for intake of dosage, dosage adherence, set alerts according to information gathered in automatic data input); automatic data input (for example: pollen levels, air pollution, weather conditions, GPS location, data from additional devices); data from additional devices (for example, connected via Bluetooth, spirometer, accelerometer, registrations of sleep and physical activity); and hands-on guidance through national service portal to a remote memory (for example, inquiry to physician, prescription, dosage adjustment, schedule clinical visits, transfer individual information of e.g. symptoms and lung function). The computer may display graphs and statistics, and visual a dosage plan.

According to one embodiment, the computer is configured to comprise three modules: Manual Data Input, Automatic Data Input and Hands-on guidance, as described above. The module Manual data input may include personal data and personalized settings for each user. In addition, the system may ask users, at regular intervals (from daily to monthly basis) to register symptoms through validated questionnaires. In Automatic data input user-generated data may be gathered from the portable spirometer together with relevant background information from external web services. Web services may provide air quality information of pollen levels, weather conditions and particle concentrations based on GPS-location or other selected location. In Manual data input, optional alerts are set in relation to poor air quality. In case of severe conditions, the system may recommend an alert to be send to a clinic through secure access of Hands-on guidance.

According to one embodiment, hands-on guidance may provide a user with information and self-management support through any national portal to any national health care system. Such service may allow for a two-way communication between user and health care professionals. Examples on how hands-on guidance may be used: automatic transfer of user's dosage plan from the primary source (medical record) to the system. This may be a treatment plan following national plans and regulations, provided by a national board of health and welfare; follow a user's medical adherence (e.g. based on manual data input); the possibility to set clinical alerts in case of impairment (symptoms, lung function, environmental factors or increased need of medication alerts signs of exacerbations); the possibility of contacting health care provider through inquiries; and transfer gathered information of biological end markers from the system for clinical evaluation.

According to one embodiment, the system may be configured for measurement of lung function in a more detailed way, and for giving the user immediate visual feedback and dosage adjustment recommendations. It may also be configured to provide a possibility of transferring information to a user's health care provider. The system may help to automate a dosage plan so that more users can have their individual dosage plans according to recommendations and, in addition, as it is provided electronically in their mobile phone, will carry it with them wherever they may need it.

According to at least one embodiment, the success of a user's self-management is depended on dedicated healthcare providers or a key individual who work closely with the treating physician. In other words, users should not be left alone, and self-management is not a goal itself that replace proactive involvement from health care professionals. The claimed system may enable evaluation of user's symptoms, lung function, intake daily medication automatic data input of user dosage plan, air quality based on particle concentrations, pollen and weather conditions. The concept also enables users to send inquiry to the clinic, schedule appointments and transfer gathered information to a clinic for hands-on guidance. Furthermore, the system may provide choice of medication and dosage adjustments. The system may reduce a burden of disease for individuals and society, reduction of emergency visits.

According to at least one embodiment, the system overcomes one or more of the problems mentioned above by supporting self-management of a disease, improving communication between patient and healthcare as well as making health care more efficient while also increasing the quality of clinical decisions. An easy-to-use self-management application with portable spirometry will enable healthcare to better follow guidelines without increasing number of visits while also reducing number of unplanned visits given that a user's dosage plan can be adapted to variable factors over time (lung function, health condition, weather, pollen count etc.) and given that a user's motivation to follow treatment will increase. It will be apparent to those skilled in the art that various modifications and variations can be made to the system and dosage regime. Especially that one or more of the embodiments disclosed above can be combined with each other to achieve the overall goals with the system. Other embodiments will be apparent to those skilled in the art from consideration of the specification and practice of the disclosed system and dosage regime. It is intended that the specification and examples be considered as exemplary only, with a true scope being indicated by the following claims and their equivalents.

The invention claimed is:

1. A computer controlled dosage system, for dosage adjustment for a mobile, handheld, inhaler for delivering a dosage of a medicine to a user, the system comprising:
 a spirometer for measuring at least lung volume;
 a handheld mobile computer of the user, separate from the inhaler, the handheld mobile computer being a mobile smart phone interoperably coupled to the spirometer and configured to communicate electronically with the spirometer to receive the measured lung volume, the handheld mobile computer being configured for a two-way communication electronically with a remote memory for sending and receiving information to and from patient medical records of the remote memory for storage in a memory of the handheld mobile computer, and the handheld mobile computer being configured to receive a manual input for storage in the memory of the handheld mobile computer, and the handheld mobile computer is further configured to receive an automatic input;

wherein the handheld mobile computer is configured to create a data set setting a plurality of levels of different dosages of medicine, by configuring a treatment plan that is established according to at least one of legislation, a national requirement and a national standard, based on the medicine used by the inhaler, the information from the patient's medical records of the remote memory, and the manual input;

wherein the handheld mobile computer is further configured to store the data set in the memory of the handheld mobile computer;

wherein the handheld mobile computer is further configured to generate an indication indicating a dosage adjustment for the inhaler, based on lung volume and on one of the plurality of levels of dosage of the data set, the indication indicating one of the plurality of levels of dosage of the data set as the dosage adjustment for the inhaler, the lung volume being the automatic input received by the handheld mobile computer;

wherein the indication is at least one of a graphic or textual display on the handheld mobile computer; and wherein the handheld mobile computer is further configured to limit the dosage adjustment such that the dosage adjustment does not result in a dangerous dosage and does not result in a non-affective dosage, thereby avoiding overmedication and undermedication.

2. The system according to claim 1, wherein the indication is at least one of a text and graphic message on a screen of the computer.

3. The system according to claim 1, wherein the spirometer is at least one of the following group: a spirometer, an accelerometer, a pulse oximeter, an impulse oscillometer (IOS), a blood sample device, a device sampling marker of inflammation, and/or a device sampling marker of inflammation from exhaled air.

4. The system according to claim 1, wherein the indication is a dosage adjustment by one of the following adjustments or by a combination of at least one of the following adjustments:
adjusting an amount of medicine delivered at each inhalation;
adjusting a frequency of inhalations;
adjusting a number of inhalations; and
adjusting by adding a further medicine.

5. The system according to claim 1, wherein the computer is a mobile phone and the configuration of the computer is an application on the mobile phone or an application in an internet cloud.

6. The system according to claim 1, wherein the automatic input is at least one of the following group: pollen levels, air pollution, weather conditions, biological parameter, pollen index, lung volume, air flow to or from lung, blood sample, blood sugar level, body weight, body surface area, environmental condition, humidity, air pressure, height above sea level, GPS position, recent or future user activity, nutrition intake, or user data.

7. The system according to claim 1, wherein the system further comprises a reminding system to communicate when a dosage should be taken.

8. The system according to claim 1, wherein the spirometer is configured to measure markers of inflammation from an airway of a user, preferably a fraction of exhaled Nitric Oxide (FeNO), and the system is configured to use this as a parameter to adjust the dosage of the inhaler.

9. The system according to claim 1, wherein the computer is further configured for providing reports or logged information regarding a user's condition based on at least one measured parameter.

10. The system according to claim 1, wherein the inhaler is configured to provide a dosage of insulin for treatment of diabetes.

11. The system according to claim 1, wherein the inhaler is selected from a group consisting of a powder dose metered inhaler, an aerosol form inhaler, a nebulised form inhaler, and any kind of dosage delivery apparatus.

12. A dosage regime for a dosage system according to claim 1, wherein a dosage of medicine is adjusted to one of the plurality of levels of dosage of the data set.

13. The system according to claim 7, wherein the communication is made via at least one of the following:
a phone;
a mobile phone;
a smartphone;
sms; and
an e-mail.

14. The system according to claim 1, wherein the system is configured to collect at least one of information and parameters from a user's electronic diary and the information from a user's electronic diary comprises past; present, and future information regarding at least one of the following group: gym visits, exercises, and location.

* * * * *